United States Patent
Sentell et al.

(10) Patent No.: US 11,062,394 B2
(45) Date of Patent: Jul. 13, 2021

(54) MORE-INTELLIGENT HEALTH CARE ADVISOR

(71) Applicant: Alight Solutions LLC, Lincolnshire, IL (US)

(72) Inventors: Randolph Sentell, Dallas, TX (US); Preston Williams, Dallas, TX (US); Jared Ashman, Dallas, TX (US); Greg Morgan, Dallas, TX (US)

(73) Assignee: ALIGHT SOLUTIONS LLC, Lincolnshire, IL (US)

( * ) Notice: Subject to any disclaimer, the term of this patent is extended or adjusted under 35 U.S.C. 154(b) by 33 days.

(21) Appl. No.: 15/289,088

(22) Filed: Oct. 7, 2016

(65) Prior Publication Data
US 2017/0103171 A1    Apr. 13, 2017

Related U.S. Application Data

(60) Provisional application No. 62/238,266, filed on Oct. 7, 2015.

(51) Int. Cl.
| | |
|---|---|
| G16H 10/00 | (2018.01) |
| G06Q 40/08 | (2012.01) |
| G16H 10/60 | (2018.01) |
| G06F 19/00 | (2018.01) |
| G06Q 30/02 | (2012.01) |

(52) U.S. Cl.
CPC ........... *G06Q 40/08* (2013.01); *G06F 19/00* (2013.01); *G06Q 30/0282* (2013.01); *G16H 10/00* (2018.01); *G16H 10/60* (2018.01); *Y02A 90/10* (2018.01)

(58) Field of Classification Search
CPC .................. G16H 10/00; G06Q 30/0282
See application file for complete search history.

(56) References Cited

U.S. PATENT DOCUMENTS

| | | | |
|---|---|---|---|
| 2008/0162496 A1* | 7/2008 | Postrel | G06Q 10/10 |
| 2010/0235295 A1* | 9/2010 | Zides | G06Q 30/02 |
| | | | 705/347 |
| 2012/0239417 A1* | 9/2012 | Pourfallah | G06Q 50/22 |
| | | | 705/2 |
| 2014/0074454 A1* | 3/2014 | Brown | G10L 15/08 |
| | | | 704/9 |
| 2016/0063215 A1* | 3/2016 | Zamer | G06F 19/3481 |
| | | | 705/3 |
| 2017/0011200 A1* | 1/2017 | Arshad | G06F 19/3456 |
| 2017/0039344 A1* | 2/2017 | Bitran | G06F 19/328 |

\* cited by examiner

*Primary Examiner* — Maria C Santos-Diaz
(74) *Attorney, Agent, or Firm* — Thompson Coburn LLP

(57) ABSTRACT

In one aspect the present disclosure implements a method for providing a personalized recommendation to a user of a health care service. In this regard, the method includes receiving a user's profile data that includes at least a location of the user, automatically prompting for and receiving a set of constraints from the user regarding their need to seek medical care, identifying a result set of medical care providers responsive to a user request, determining whether the result set satisfies the imposed constraints, and if the result set satisfies the imposed constraints, creating, in real-time, a list that identifies at least one medical care provider from the result set for display to the user.

36 Claims, 11 Drawing Sheets

MORE-INTELLIGENT HEALTH CARE ADVISOR

CROSS-REFERENCE TO RELATED APPLICATION

This application claims the benefit of U.S. Provisional Application No. 62/238,266, entitled "More-Intelligent Health Care Advisor" filed Oct. 7, 2015, which is hereby incorporated by reference.

BACKGROUND

A typical health care system includes a variety of participants, including doctors, hospitals, insurance carriers, employers, and patients, among others. In this regard, an insurance carrier can offer a variety of health plans to customers (i.e., individuals, corporate entities, or other organizations). The customer of the carrier pays a fee for health care insurance that serves as a hedge against the risk of incurring future medical expenses. Unfortunately, the cost of insurance and associated medical expenses is growing at a faster rate than other goods and services in the economy. This growth in cost continues despite enormous efforts being expended to improve the health care system. To this end, it is in the best interest of insurance carriers and their customers to minimize outlays for medical expenses. By doing so, corresponding savings may be achieved in the costs of the insurance and a patient's out-of-pocket expenses. Yet, the modern health care system in which these various stakeholders participate has become increasingly expensive and complex. Government regulation and other oversight adds to this complexity as does advances in care options that are designed to ensure proper patient diagnosis and treatment.

Consumers and other stakeholders in the health care system have long sought better access to information regarding the relative cost and quality of care. However, the tools and information available in the market today fall far short and there is a robust need to enable more informed decision-making. In this regard, the rapid adoption and growth of consumer-directed health plans that encourage beneficiaries to choose providers and treatments based on relative cost and quality makes it even more critical that consumers have information for comparing health care alternatives. Many consumers now have high-deductible insurance where they are responsible for managing out-of-pocket expenses up to the limits of the deductible. In a number of ways, health care has substantial differences from other industries that provide products and services to the public. One of the major differences is the complexity of health care brought about because of its terminology, processes, and pricing dynamics. These factors in health care's complexity are not intuitive for most people and may never be easily understood by some. In addition, medical care is extraordinarily personal with each individual having different medical needs, history, options, coverage, and preferences. When it comes to navigating the health care landscape, every individual's situation is largely unique. On the other hand, health care, like any other product or service, health care can and should be measured based on relative cost and quality. The results, in turn, may be shared with those who consume and purchase health care to create a more competitive and accountable marketplace. With the proper tools, this marketplace would then enable consumers to make more-fully informed choices regarding their health plans, providers, and treatments.

SUMMARY

This Summary is provided to introduce a selection of concepts in a simplified form that are further described below in the Description. This Summary is not intended to identify key features or essential features of the claimed subject matter, nor is the Summary to be used as an aid in determining the scope of the claimed subject matter.

In one aspect, the present disclosure implements a method for providing a personalized recommendation to a user of a health care service. In this regard, the method includes receiving a user's profile data that includes at least a location of the user, automatically prompting for and receiving a set of constraints from the user regarding their need to seek medical care, identifying a result set of medical care providers responsive to a user request, determining whether the result set satisfies the imposed constraints, and if the result set satisfies the imposed constraints, creating, in real-time, a list that identifies at least one medical care provider from the result set for display to the user.

DESCRIPTION OF THE DRAWINGS

The foregoing aspects and many of the attendant advantages will become more readily appreciated as the same become better understood by reference to the following detailed description, when taken in conjunction with the accompanying drawings, wherein.

DESCRIPTION

The description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

System Environment

The present invention may be embodied as a system, method or computer program product. The present invention may take the form of a hardware embodiment, a software embodiment or a combination of software and hardware. Furthermore, the present invention may take the form of a computer program product embodied in any tangible storage medium of expression having computer-usable program code embodied in the medium. The computer-usable or computer-readable medium is not a transitory signal per se, and is any tangible medium that can contain and store the program for use by or in connection with an instruction execution system, apparatus, or device.

Figure 1:
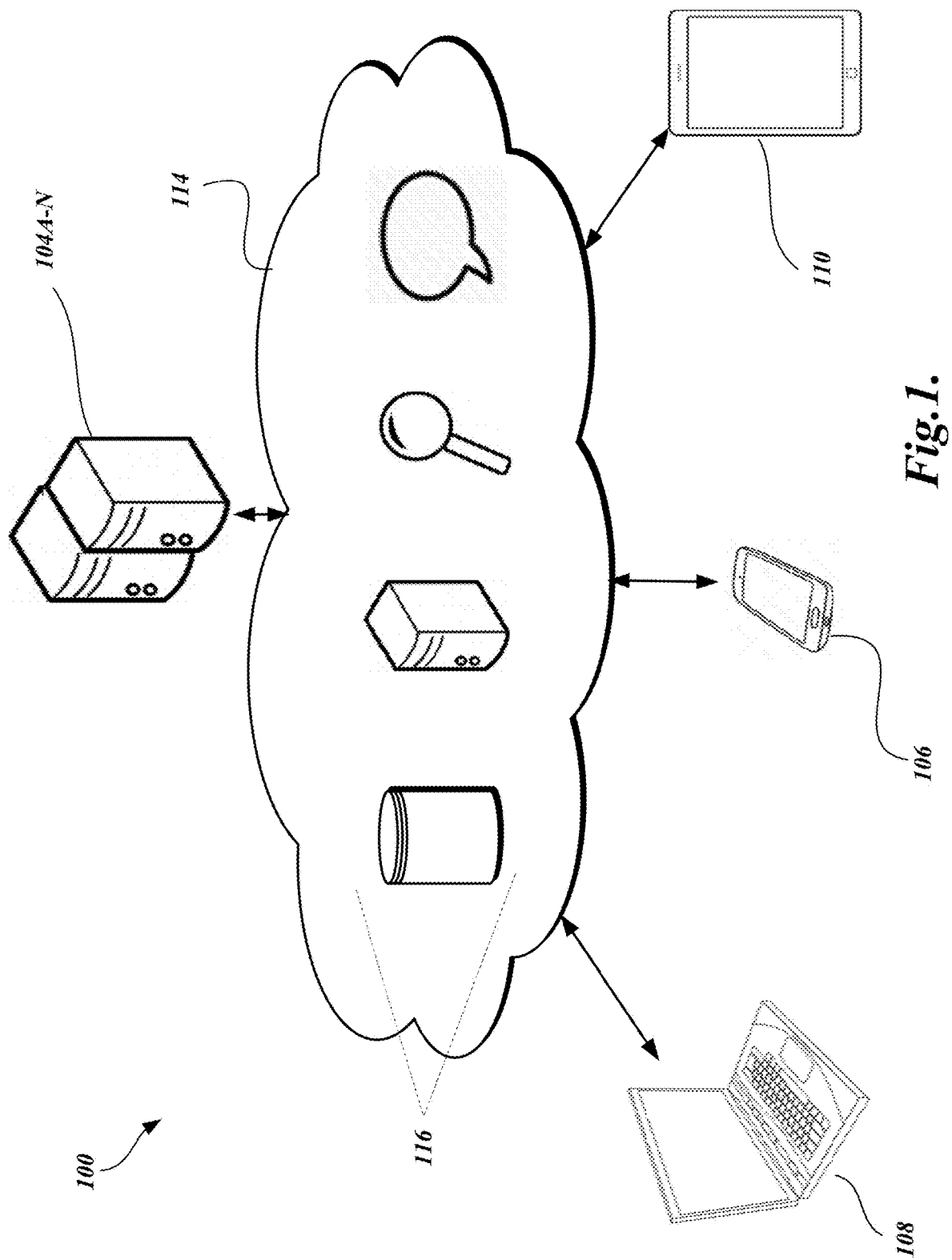
FIG. 1 is a block diagram depicting an exemplary cloud computing environment where described embodiments of the disclosed subject matter can be implemented.

Referring to FIG. 1, the following is intended to provide an overview of a cloud computing environment 100 in which aspects of the present invention may be implemented. Cloud computing is a computing model that enables convenient, on-demand network access to a shared pool of configurable computing resources, e.g., networks, servers, processing, storage, applications, and services, that can be provisioned and released rapidly, dynamically, and with minimal management efforts and/or interaction with a service provider. In embodiments, one or more aspects, functions and/or processes described herein may be performed by the backend servers 104A-N or client computing devices 106-110 within the cloud computing environment 100. In embodiments, the backend servers 104A-N can be a standalone server or multiple computing devices, which implement backend processes of the present invention within a networking environment 100. The backend servers 104A-N and the services that they provide can be integrated into the networking environment of any enterprise. Additional description of the backend servers 104A-N will be provided below with reference to FIG. 2.

The computing environment 100 depicted in FIG. 1 also includes a plurality of client computing devices associated with a user including the mobile phone 106, the laptop computer 108, and the tablet 110. In this regard, the backend servers 104A-N are configured to communicate with the mobile phone 106, the laptop computer 108, and the tablet 110 or any other computing device via the network 114, which may be implemented as a local area network ("LAN"), wireless network, wide area network ("WAN"), such as the Internet, and the like. As known to those skilled in the art and others, the computing devices illustrated in FIG. 1 may be configured to exchange files, commands, and other types of data over the network 114. However, since protocols for network communication, such as TCP/IP, are well-known to those skilled in the art, those protocols will not be described here.

As depicted in FIG. 1, the cloud computing environment 100 includes cloud resources 116 that are made available to the backend servers 104A-N and the computing devices 106-110 via the network 114. Cloud resources 116 can include a variety of hardware and/or software computing resources, such as servers, databases, storage, search services, networks, applications, messaging services, and platforms as shown, for example, in FIG. 1. Cloud resources 116 may be on a single network or a distributed network across multiple cloud computing systems and/or individual network-enabled computing devices. In this regard, cloud resources 116 are typically provided and maintained by a service provider so that other computing devices in the networking environment 100 do not need to maintain resources on a local device. In embodiments, cloud resources 116 may include one or more computing devices that are specifically adapted to perform one or more of the functions and/or processes described herein.

In one aspect, the present disclosure provides functionality to generate hyper-personalized recommendations for the user regarding their health care services. Such recommendations may comprise, for example, identifying a specific doctor that satisfies certain criteria of the user. More generally, the recommendations and information provided by the present disclosure utilizes a vast array of resources and data. Prior health-care activity, claims data, insurance data may be accessed and utilized by the service provided by the present disclosure. This data is processed and used to enable consumers to make more-fully informed choices regarding their health plans, providers, and treatments. The backend servers 104A-N utilizing the cloud resources 116 may be considered as a system capable of generating health care recommendations and related services for the one or more users associated with the computing devices 106-110. It is to be appreciated here that the user and health care data may evolve continuously and the system provided by the present disclosure is able to capture and reflect this dynamic behavior of the data sets. The recommendations may further be personalized from user-to-user in a number of ways as will be described in further detail below.

Figure 2:
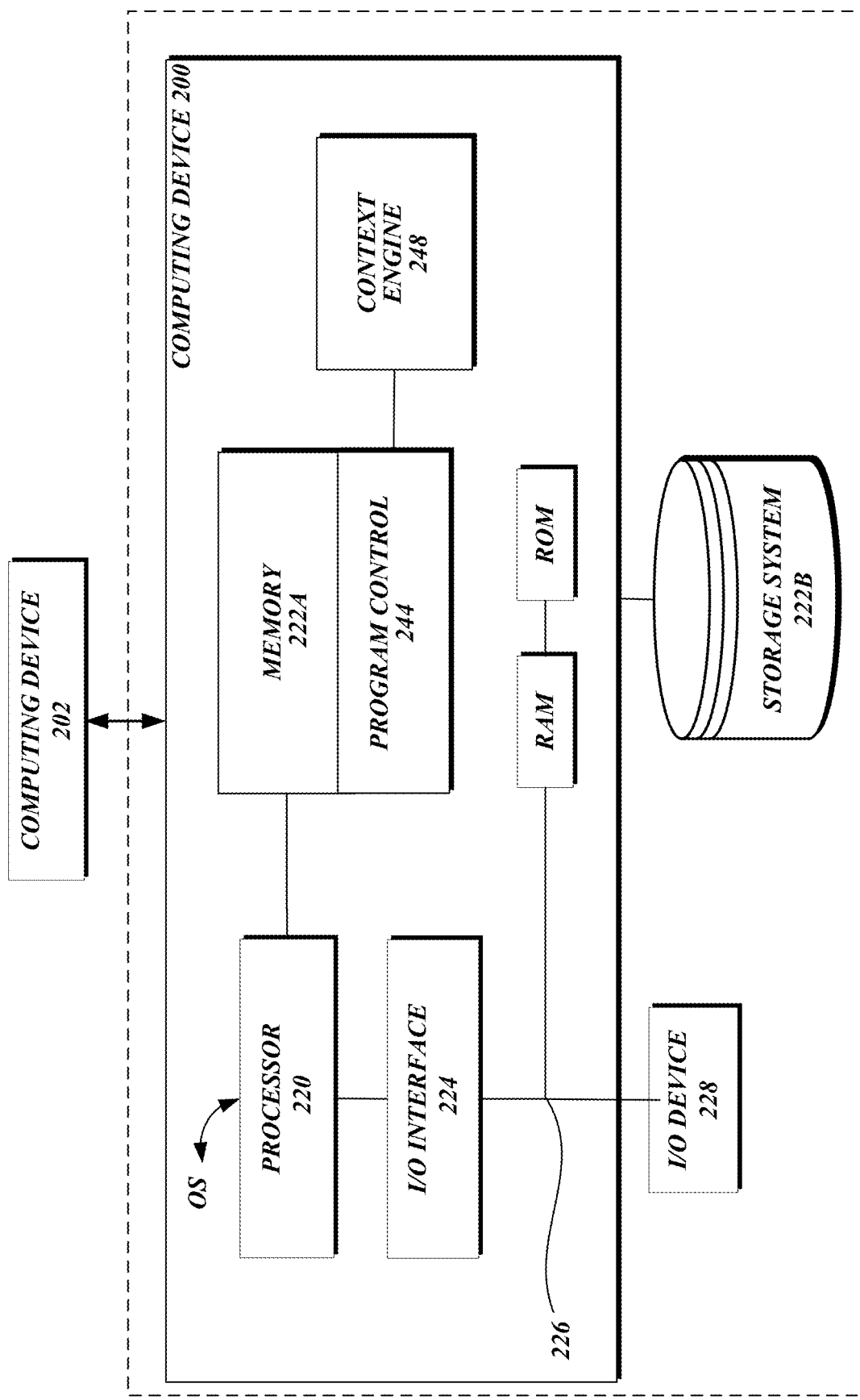
FIG. 2 is a block diagram illustrating the components of a computing device configured to provide health care recommendations in accordance with the present disclosure.

Now with reference to FIG. 2, additional description will be provided regarding the backend servers 104A-N (FIG. 1) provided by the present disclosure. In embodiments, the servers 104A-N can be a standalone server, which implements the processes of the present invention within a networking environment. The backend servers 104A-N includes a computing device 200 which can be resident on a network infrastructure. As shown, the computing device 200 includes a processor 220 (e.g., a CPU), a memory 222A, an I/O interface 224, and a bus 226. The bus 226 provides a communications link between each of the components in the computing device 200. In addition, the computing device 200 includes a random access memory (RAM), a read-only memory (ROM), and an operating system (O/S). The computing device 200 is in communication with the external I/O device 228 and a storage system 222B. The I/O device 228 can comprise any device that enables an individual to interact with the computing device 200 (e.g., user interface) or any device that enables the computing device 200 to communicate with one or more other computing devices (e.g., devices 106-110, etc.) using any type of communications link.

The processor 220 executes computer program code (e.g., program control 244), which can be stored in the memory 222A and/or storage system 222B. In embodiments, the program control 244 of the computing device 200 provides a Context Engine 248, which comprises program code that is adapted to perform one or more of the processes described herein. The Context Engine 248 can be implemented as one or more program code in the program control 244 stored in memory 222A as separate or combined modules. Additionally, the Context Engine 248 may be implemented as separate dedicated processors or a single or several processors to provide the functions described herein. While executing the computer program code, the processor 220 can read and/or write data to/from memory 222A, storage system 222B, and/or I/O interface 224. In this manner, the program code executes the processes of the present disclosure.

The program code can include computer program instructions that are stored in a computer-readable storage medium. The computer program instructions may also be loaded onto a computer, other programmable data processing apparatus, or other devices to cause a series of operational steps to be performed on the computer. Moreover, any methods provided herein in the form of flowcharts, block diagrams or otherwise may be implemented using the computer program instructions, implemented on the computer-readable storage medium. The computer-readable storage medium comprises any non-transitory medium per se, for example, such as electronic, magnetic, optical, electromagnetic, infrared, and/or semiconductor system. More specific examples (a non-exhaustive list) of the computer-readable storage medium include: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any combination thereof. Accordingly, the computer-readable storage medium may be any tangible medium that can contain or store a program for use by or in connection with an instruction execution system, apparatus, or device of the present invention.

According to aspects of the invention, the Context Engine 248 communicates with and enables the users of the computing devices 106-110 (FIG. 1) to receive recommendations and other information regarding their health care services. In this regard, examples of an interface executed on a client computing device which interacts directly with end users will be described in further detail below with reference to FIGS. 3-10. In another embodiment, a workflow is provided that enables human advisors to provide health care recommendations to end users. A human advisor utilizing the computing device 202 may interact with the Context Engine 248 for the benefit of another person. Accordingly, the end user may be a caller or participant in an instant message session seeking health care recommendations from the human advisor who accesses the functionality provided by the present disclosure. The advanced workflow features of the Context Engine 248 enables the human advisor to provide these recommendations. To this end, the human advisor may be an enterprise employee or other personnel who is authenticated and trained to provide recommendations regarding a user's health plans, providers, and treatments.

By working with a number of end users, human advisors obtain domain knowledge regarding various health care issues. In some aspects of the present disclosure, systems and/or methods are provided for accessing and updating a knowledge base of health care and/or experience information maintained by the Context Engine 248. The human advisors may receive, from potentially multiple sources, various pieces of information that could be relevant to users. The advanced workflow provided by the present disclosure enables the human advisors to tag and annotate issues for recording in the knowledge base. These issues may be annotated at substantially the same time as issues are received from a source. In this regard, human advisors may provide feedback to the Context Engine 248 which represents a piece of domain knowledge that was learned in providing a health care recommendation or otherwise. As described further below, this feedback may be used by the Context Engine 248 to provide health care recommendations to other, similarly situated users. In this regard, the systems provided by the present disclosure include multiple clients in communication with a server that provides functionality for accessing and updating the knowledge base utilized by human advisors. The incoming issues may be processed, tagged, and annotated in various ways when received. Then, the advanced workflow enables issues to be recalled from the knowledge base when they are contextually relevant. As such, the present disclosure provides a knowledge base service that enables tagging and access to contextually relevant from multiple clients within a networking cloud architecture.

As described below with reference to FIGS. 3-10, the Context Engine 248 is configured to provide health care recommendations through an application on a computing device such as a mobile phone. However, it should be well understood that the examples provided below should be construed as exemplary and a mobile application is just an exemplary embodiment. Instead of interacting with a user via a mobile application, other embodiments are possible. For example, the functionality of the Context Engine 248 provided by the present disclosure could be exposed through an Application Programming Interface (API) and accessed in machine-to-machine communications. In this regard, the functionality provided by the present disclosure could be accessed within other network applications such as Customer Relationship Management (CRM) system or human resource software. More generally, aspects of the present disclosure may be accessed using any number of different types of interfaces including, but not limited to applications, a text or speech based natural language interface, reporting applications, a web interface, email, and messaging platforms (i.e. text messaging, Facebook messenger, Twitter, and the like) among others. Accordingly, the utilization of a mobile application as described herein is merely exemplary and the present invention could be implemented in other ways than those described.

Exemplary Mobile Application

Now with reference to FIGS. 3-10, a mobile application that provides users with contextually relevant health care information will be described. It should be well understood that the examples provided below with regard to the mobile application and its' user interface should be construed as exemplary. As described above, the functionality of the Context Engine 248 (FIG. 2) is interface agnostic and a client application is just one way in which the present disclosure may interact with users in a networking environment. Now with reference to FIG. 3, one exemplary graphical user interface provided by the application is shown with user interface elements suitable for illustrating various aspects of the present disclosure. In the exemplary embodiment depicted in FIG. 3, a home screen 300 is displayed that includes the "HOW CAN WE HELP" search box 302, the "I NEED HELP WITH" drop down menu 304 and the activation cards 306, 308, and 310. In general, the user interface elements utilized by the present application (i.e., menus, toolbars, drop-down boxes, search boxes, activation cards, and the like) such as those depicted in FIG. 3 provide convenient ways of interacting with the user.

Figure 3:
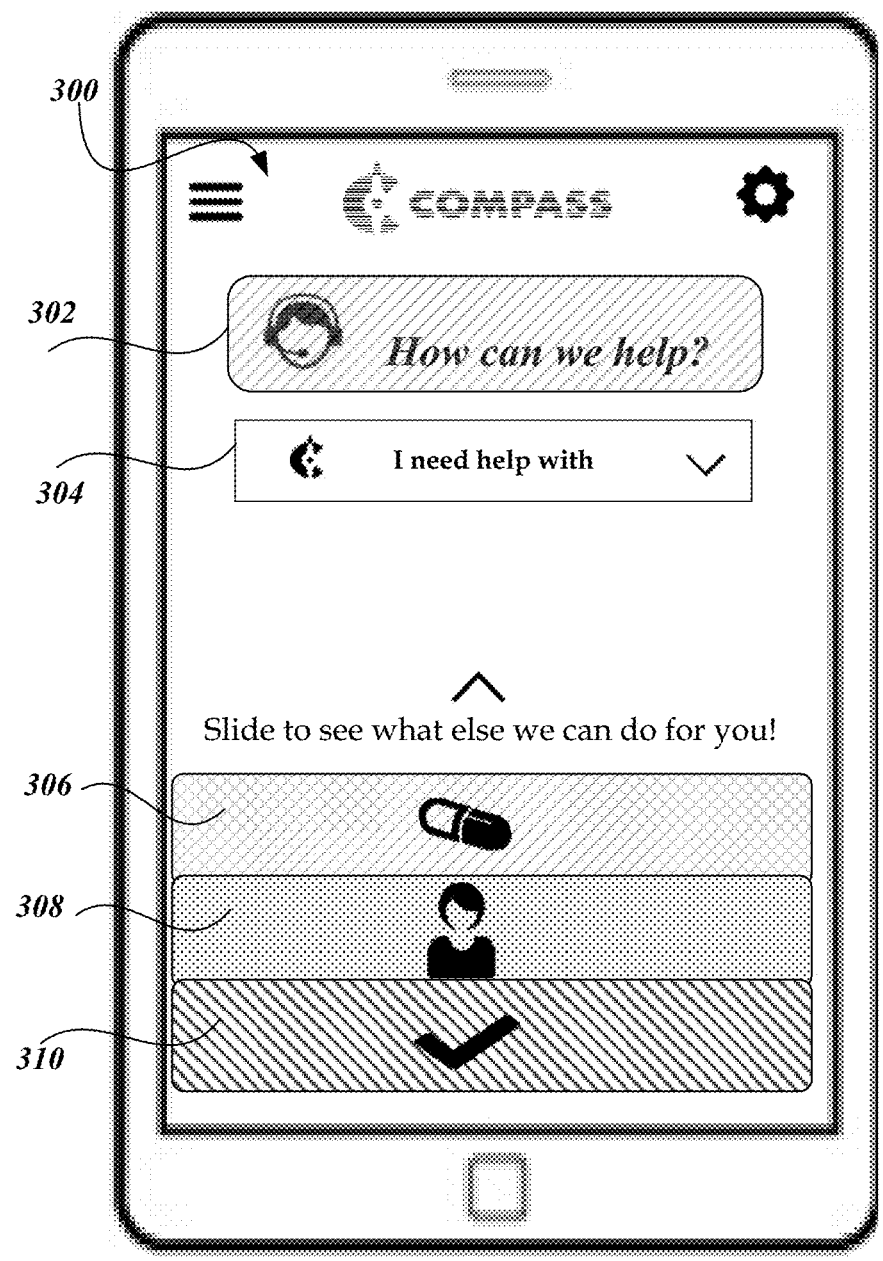
FIG. 3 is a pictorial depiction of an exemplary user interface for interacting with a user obtaining health care information in accordance with the present disclosure.
Figure 4:
FIG. 4 is a pictorial depiction of an exemplary user interface for interacting with a user obtaining health care information in accordance with the present disclosure.

The Home Screen 300 depicted in FIG. 3 enables a user to make various selections to navigate through the application and access desired functionality. In one aspect, the "HOW CAN WE HELP" search box 302 enables a user to provide text input representing a search query. Conveniently search queries and results are saved and can be recalled by a user or health care advisor through various interfaces. Also, previously conducted searches and results can be updated with results changing based on the current context of the search and/or providers. Thus, the "HOW CAN WE HELP" search box 302 provides a readily-understandable mechanism for a user to initiate a search that is saved by the system and may be subsequently recalled/deleted.

In some embodiments, a user completes a "Get Connected" process using the application provided by the present disclosure. For example, a "Welcome Page" (not shown) may be presented in response to the selection of the activation card 310 (FIG. 3) that directs a user to enroll in their employer health care program. To register, the user creates an account by providing information to the system which becomes the basis of a user profile. In this regard, the "Get Connected" process may include prompting the user to enter information such as name, age, gender, date of birth, address, telephone number, medications, doctors, prior procedures, conditions, permission to access claims information, health insurance data, medical information, and the like. As part of the "Get Connected" process, the user may also be prompted to provide personal preferences for health care providers, such as location, years of experience, gender, specialty, reputation, language spoken, health plan and hospital affiliations, etc. User preferences are unconstrained and can be completely personalized. As will be understood by one skilled in the art, this user profile data may be stored in a profile database maintained by the system storage 222B (FIG. 2) or a cloud resource 116 (FIG. 1). In alternative embodiments, user demographic information may be obtained automatically by accessing existing data stores thereby eliminating or minimizing the manual entry of data.

In an exemplary scenario, a user provides input regarding their current medications during the "Get Connected" process indicating that, for example, the user consumes Nexium once per day. For example, the user may be directed to the medication screen 400 depicted in FIG. 4 which includes the text input box 402 and activation buttons 404 and 406. The text input box 402 is configured to populate the most relevant medications as the user types and enables the user to identify a medication (i.e. Nexium). Subsequent screens allow the user to identify the dosage and usage frequency information for their prescription. By providing the appropriate input, the user is able to input all of their medication information into the system. Other user preference and demographic information may be obtained during the "Get Connected" process or subsequently in the same or substantially similar way.

Aspects of the present disclosure may access and utilize various types of data about the user to proactively provide recommendations. In this regard, filtering a user's input or other data may be performed to capture the attributes or feature sets of the users medications which may be compared to various alternatives. In the example depicted in FIG. 3, a user that completed the "Get Connected" process may be presented with the "Pill" activation card 306. The presentation of the "Pill" activation card 306 represents a visual cue indicating that there is proactive message from the system relevant to the user's health care. In this regard, a proactive message may be provided in the form of an activation card by the present invention in a number of different instances. By way of example, a cost estimate is typically communicated to the user regarding upcoming procedures. Also, a doctor recommendation is provided in instances when a user has not established a primary care doctor. If a health care provider does not meet quality or cost thresholds, a recommendation for one or more alternative care providers may be proactively communicated to the user. One skilled in the art and others will recognize that these are just examples and that other types of proactive message can and typically will be communicated.

Figure 5A:
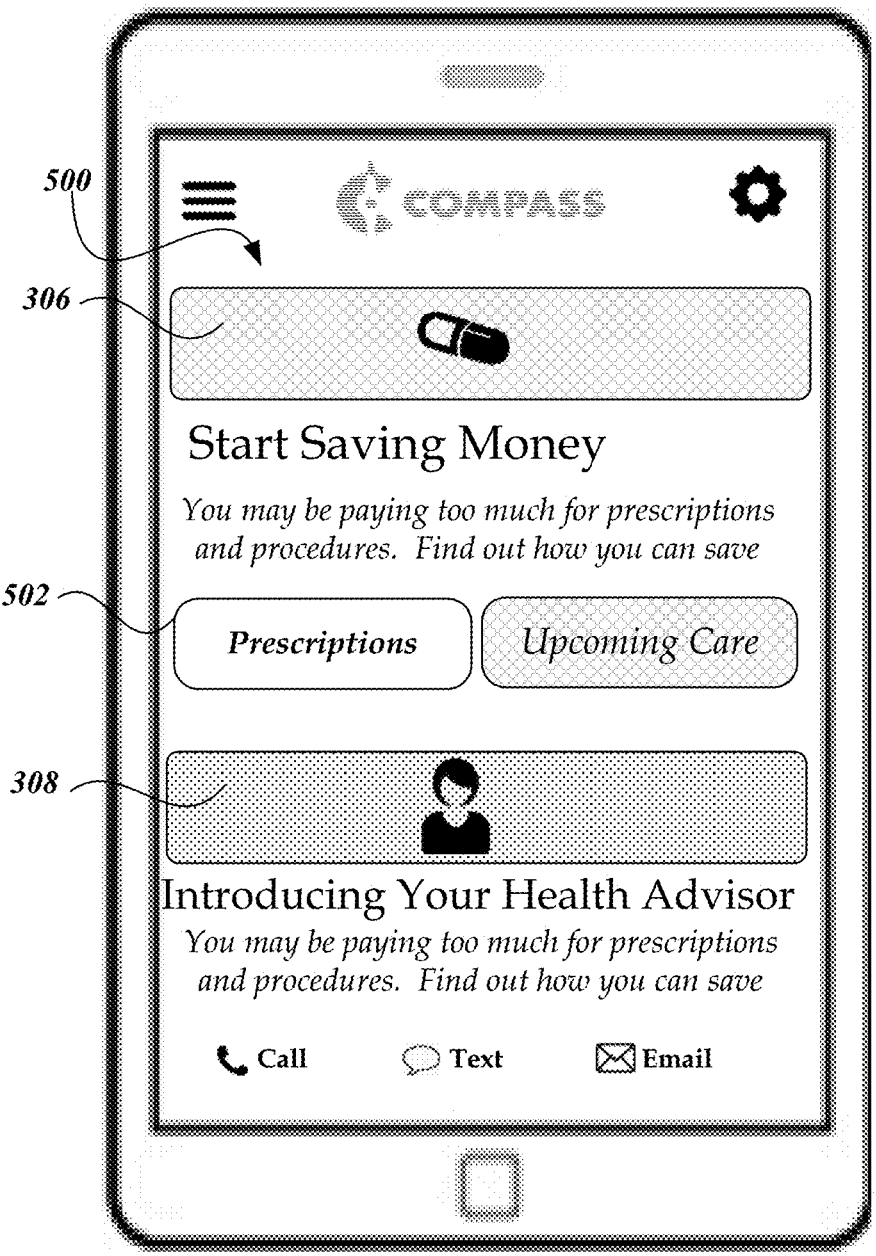
FIG. 5A is a pictorial depiction of an exemplary user interface for interacting with a user obtaining health care information in accordance with the present disclosure.

Now with reference to FIG. 5A, an exemplary screen 500 suitable for illustrating aspects of the present disclosure is shown. In the scenario described above, the user is presented with the "Pill" activation card 306 (FIG. 3) after completing the "Get Connected" process. A user may select the "Pill" activation card 306 in order to obtain additional information and navigate the application. In this instance, expansion of the "Pill" activation card 306 results in a message being displayed that reads: "Start saving money." Selection of the button 502, in this example, may result in a message being displayed which states that the user may be able to save as much as $1200 a year on their Nexium prescription by using a lower-cost alternative medication (e.g., Pantoprazole or Omeprazole). Also, since the user in this example is interested in the alternative medications, the "Health Advisor" card 308 may be expanded. With the expansion of the "Health Advisor" card 308, a convenient mechanisms is provided for contacting the user's health care advisor so that additional information may be obtained about the alternative medications.

In general and according to one aspect, the present invention provides proactive messaging and user interface cues to promote better decision-making. As shown in FIGS. 3 and 5A, various types of activations cards may be presented to the user. The system may determine which activation cards, visual cues, and/or alerts are displayed based on actions that a user is scheduled to perform. More generally, activation cards can represent various types of notifications such as, but not limited to alerts, proactive messages, calls to action, and/or micro-targeted information sources that reflect a specific issue known about the user. Moreover, the determination regarding which activation cards are presented at a given point in time is made based on multiple factors such as, but not limited to progress against incentives or "Get Connected" information, follow-up care for known procedures or diagnoses, prior solution activity, information derived from claims, user education, demographics, among others.

Now with reference again to the Context Engine 248 described above with FIG. 2, additional aspects of the present disclosure will be described. In one aspect, the Context Engine 248 provides an autonomous recommendation system that generates dynamic, personalized offerings regarding a user's health care based on real-time information. As such, the Context Engine 248 automates the process of identifying the user's health care needs, interests, and preferences based, at least in part, on the user's current and/or historical information. This health care data may be obtained directly from user input or obtained from other sources such as a user's insurance claim data. In this regard, the user data may be processed to generate a user profile, which may further vary dynamically based on user's on-going health care information.

In another aspect of the present disclosure, human advisors obtain and memorialize domain knowledge regarding various health care issues. As mentioned previously, a workflow provided by the present disclosure enables the human advisors to tag and annotate issues for recording in the knowledge base maintained by the Context Engine 248. In this regard, a trigger may be defined within the Context Engine 248 to provide recommendations to users that satisfy certain criteria as defined in their user profile. By utilizing the domain knowledge of human advisors and defining triggers in this way, the system is able to provide real-time dynamic, context-driven, hyper-personalized recommendations that satisfy a specific user's health care needs.

Selecting a physician or other health care service provider can be a daunting task for most people. Some factors to consider when choosing a physician include reputation, location, gender, specialty, language spoken, health plan and hospital affiliations, etc. Many solicit recommendations from friends and family members, and others consult the database of their state's medical board. To add to the complexity, the health care insurance coverage can largely contract the pool of providers. There are different types of health insurance plans designed to meet different needs of individuals and families. Some types of plans restrict provider choices or give preference to providers who belong to the plan's network of doctors, hospitals, pharmacies, and other medical service providers. Some plans require the patient to pay a greater share of costs for providers outside the plan's network. What is desirable is a comprehensive system that helps to optimize and streamline the interface and interaction between patients and all of the doctors, or between users and all of their service providers.

Now with reference to FIG. 5B, a method 550 configured to gather information and provide health care recommendations will be described. In this regard, the method 550 is described in conjunction with a mobile application configured to provide users with a recommendation of a health care provider. Aspects of the mobile application and its' user interface are referenced at certain relevant points within the discussion of the method 550. In according to one aspect, the present disclosure is configured to gather a vast amount of information about a substantial number health care providers and their services. As mentioned previously, this "provider data" may be obtained by health care advisors and memorialized in a knowledge base. Moreover, this knowledge base of "provider data" is regularly updated as the human advisors provide certain services to users as described above.

Figure 5B:
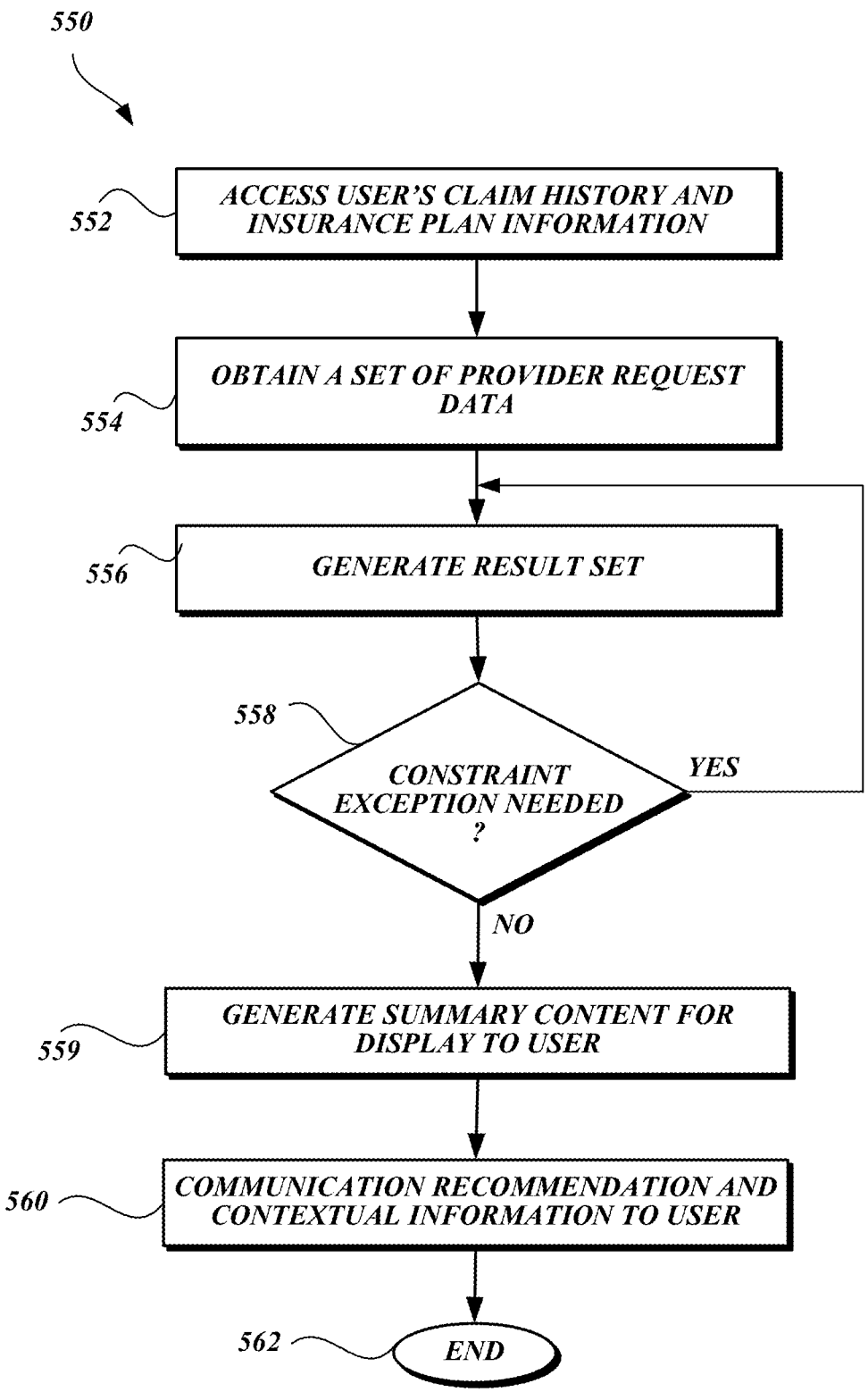
FIG. 5B is an exemplary method for obtaining user data and providing a recommendation of a health care provider in accordance with the present disclosure.

As shown in FIG. 5B, the method 550 begins at block 552 where a set of information about the user is obtained by the system provided by the present disclosure. In one aspect and as described previously, a user completes a "Get Connected" process in order to enroll in an employer-sponsored health care program. As part of the "Get Connected" process, the method 550 obtains at least a set of demographic information (age, gender, date of birth, address, health insurance information) about the user. With the demographic information, the method 550 can access two other types of information that are used in the process of making health care recommendations. First, aspects of the present disclosure are able to access and gather a user's "claim and history information" at block 552. This set of information includes the user's medical claims and associated history of medical services. Second, aspects of the present disclosure are able to access and gather a user's "insurance and other benefit information" which identifies the various benefits and ancillary service programs (i.e., telemedicine, weight loss/diabetes programs, and the like) available to the user, at block 552. Typically, aspects of the present disclosure are able to access and gather a user's (1) claim and history information, and (2) insurance information, at block 552, from an insurance provider database. In other instances, certain information may be obtained by prompting the user if that information is not available from an insurance provider. For example, a user may be prompted for their current or past doctors or any other piece of information if that information does not exist or is not available from an accessible database.

At block 554 of the method 500, a set of "provider request" data is obtained by aspects of the present disclosure. In general and in accordance with one embodiment, users may be taken through a decision tree of questions and responses to obtain specific information about the user's needs and preferences in seeking medical care. The user may provide this information, at block 554, in order to find a medical care provider that is available and qualified to provide certain medical services. Significantly, aspects of the present disclosure may issue a number of variable questions to gather certain contextual information before a recommendation is provided. In generating appropriate questions, the previously obtained data including a user's previous input, medical history, and insurance data may be employed to drive question content and flow. Accordingly, the variable questions that are asked before a recommendation is provided account for a user's specific provider needs, medical history, preferences, existing doctors, existing conditions, user demographics, insurance, third-party benefits, and timing. Moreover, the question content and flow can intelligently direct users to more-appropriate options given their circumstances. For example, if a user asks for a dermatologist to treat a rash, the present disclosure may generate a query asking whether the user would prefer to visit a primary care physician since a practitioner would be available sooner and the user could be treated at a lower cost. As another example, if a user searches for a doctor to perform a knee surgery, a question could be generated asking whether costs for a knee surgery should be provided. By intelligently identifying question content and directing flow in this manner, highly relevant data is obtained from the user. This enables aspects of the present disclosure to insure that highly relevant data is input into the context engine 248 in order to identify a medical care provider well-suited for satisfying the user's medical needs. Additional detail and specific examples of the "provider request" data obtained at block 554 are described below with reference to FIG. 6.

At block 556 of the method 500, a result set of medical care providers responsive to a user request is generated. In accordance with one embodiment, the present disclosure provides a rules and ranking-based system to identify the most relevant medical care providers that will be recommended. To produce the result set, at block 556, multiple information sources are utilized. Similar to an Internet search engine or indexing system, each data point relevant to recommending a health care provider is tagged and potentially weighted. The Context Engine 248 provided by the present disclosure may then rank the identified medical care providers according to an estimation of their relevance or "best fit" for a particular user accounting for the previously gathered data. By way of example, a number of factors such as a medical care providers' pricing, distance to user, positive/negative feedback, years of experience, or any other data item may be used to identify the most relevant and appropriate health care providers. The Context Engine 248 may rank the medical care providers according to an estimation of their relevance, making it possible for the user to quickly identify and select the most-appropriate provider.

In generating a recommendation, certain rules are utilized to constrain the result set. Stated differently, all of the different health care providers tracked by the present disclosure are not ranked in response to a user query. Instead, constraints are implemented that initially filter certain providers from being included in the result set. For example, a health care provider whose services would not be covered by a user's insurance or does not perform a requested procedure may be eliminated from being considered. By way of another example, a doctor who has been identified as being suspended from practice or is under medical board review may be initially eliminated from consideration. More generally, the recommender system provided by the present disclosure is one that uses certain contextual data to initially constrain the result set. One skilled in the art and others will recognize that these are just some examples of some ways in which the result set may be constrained.

As further illustrated in FIG. 5B, at decision block 558 a determination is made regarding whether a constraint exception needs to be applied to the result set generated at block 556. Existing recommendation systems frequently employ a list, sort, and filter approach to identify and rank relevant items. For a number of reasons, this approach is less than optimal for providing recommendations of health care providers. Instead, aspects of the present disclosure approaches the problem of identifying the most relevant health care providers in a way that is similar to the how a human thinks about and conducts a search. A result set of health care providers that satisfies the user's criteria is initially identified. In some instances, this identified result set is sufficient such that potentially multiple health care providers satisfy all of the necessary criteria. In other instances, the identified result set may not, for example, identify any health care service providers that satisfy the user's criteria. Lets assume that a user residing in a rural area learns from a primary care physician that the user needs to visit a nephrologist. In accessing the application provided by the present disclosure, the user enters all the search criteria including a preference that the health care prover be within a twenty-five (25) mile radius of the user's residence. In this exemplary scenario, the recommender system provided by the present disclosure determines, in generating the result set at block 556, that a nephrologist does not practice within the specified twenty-five (25) mile radius. However, a constraint exception may apply in this instance such that the user is delivered to an interstitial screen (FIG. 7) which notes that there aren't any nephrologists within a twenty-five (25) mile radius who are in the network established by the user's medical plan. Then, the user is directed to the results screen where two in-network nephrologists that are within a one-hundred 100 mile radius are identified. In this instance, an exemplary constraint exception is applied to generate a result set. Accordingly, at block 558 a determination is made regarding whether a constraint exception applies to the result set generated at block 556. In instances when a constraint exception applies, the method 550 proceeds back to block 556 where a new result set using potentially modified constraints is generated. In instances when a constraint exception does not apply, the method 550 proceeds to block 559 described below.

The actions taken at blocks 556-558 are depicted in FIG. 5B as being performed in an iterative process where a result set is generated at block 556. Then, a determination is made at block 558 regarding whether a constraint exception needs to be applied to the result set generated at block 556. If a constraint exception needs to be applied and the result of the test performed at block 558 is "YES", the method 550 as depicted in FIG. 5B proceeds back to block 556. Then, the method 550 iterates between blocks 556-558 until a constraint exception does not need to be applied and the result of the test performed at block 558 is "NO". In another embodiment, the information generated at block 556 includes generating multiple result sets, namely, (1) a first preferred result set that utilizes model constraints to filter potential medical care providers, and (2) one or more alternative result sets that utilize alternative constraints to filter the medical care providers. The alternative constraints could be established based on knowledge regarding those constraints that excessively restrict the result set to too few medical providers or narrow scope of a scope. Accordingly, the process of generating a result set, at block 556, may include generating multiple result sets, each with different but intelligently identified constraints. In this instance, the test performed at block 558 may involve identifying the most appropriate result set among the alternatives to display to the user at block 559.

At block 559, a summary content that provides important contextually relevant data about a recommendation is identified and communicated to the user. An exemplary embodiment of this aspect of the present disclosure that identifies and displays summary content is described below especially with reference to FIG. 7. In one embodiment, the summary context that is presented to the user accounts for a package of potential recommendations. For example, if the request was for the cost knee surgery cost, the summary content could state, "The average cost for knee surgery in your area is $2000. Be careful not to overpay." If a single medical care provider satisfied user preferences, the summary content could state, "We only found 1 doctor that met your preferences, but there are 2 others we think you should consider." In a third example, if no recommendations were found, the summary content could state "I don't have any recommendations in your nearby area. Let's get you to a Health Advisor who can help you find the care you need." In general, identifying which pieces of summary content to communicate includes analyzing certain inputs such as user's needs and preferences in seeking medical care. This user specific information is merged with detailed cost, quality, practice pattern, experiential, and demographic information of local providers in the result set. These different data items that are relevant to identifying one or more pieces of contextually relevant data are tagged and potentially weighted. The Context Engine 248 provided by the present disclosure may then rank the available pieces of contextually relevant data according to an estimation of their relevance to a particular user. Once ranked, one or more pieces of relevant data may be communicated to the user as described more in the examples provided below.

At block 560, a recommended list of health care providers relevant to a user's query and contextually relevant information is communicated to the user. Since the communication of one more recommended health care providers and associated contextual information will be described below with reference to FIGS. 7-10, additional description of this aspect of the present disclosure will not be provided here. Then, the method 550 proceeds to block 562, where it terminates.

Figure 6:
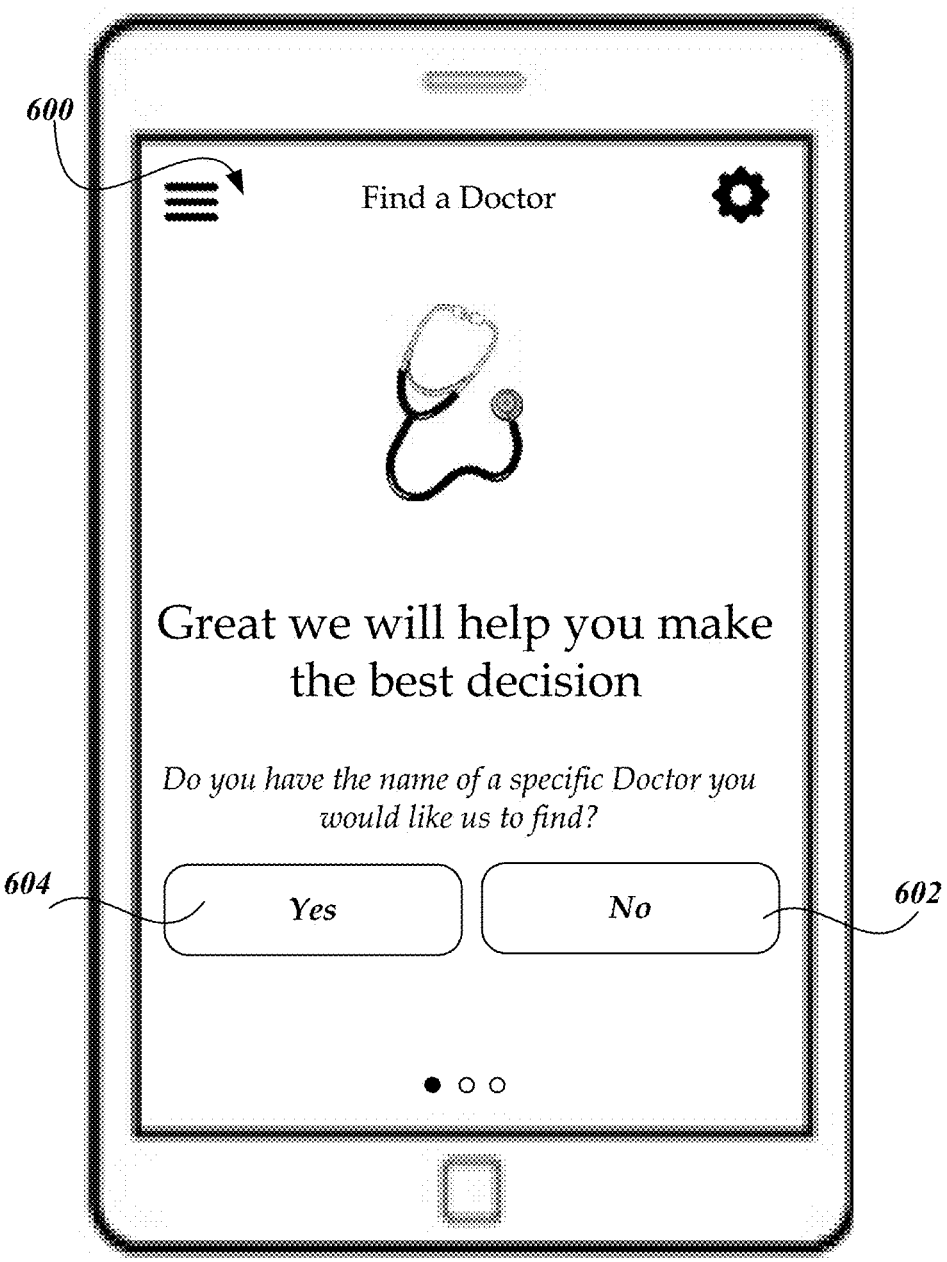
FIG. 6 is a pictorial depiction of an exemplary user interface for interacting with a user obtaining health care information in accordance with the present disclosure.

Now with reference to FIG. 6, an exemplary "Find a Doctor" screen 600 suitable for illustrating additional aspects of the present disclosure is shown. The user could navigate to the "Find a Doctor" screen 600 by selecting a "Find a Doctor" menu item (not shown) from the "I NEED HELP WITH" drop down menu 304 that was described above with reference to FIG. 3. In one embodiment, the "Find a Doctor" screen 600 initiates the process of taking users through a dynamic, yet readily-understandable, decision tree of "triage" questions and responses that gathers specific information about the user's needs and preferences. In other words, the questions that are presented to the user are dependent on answers that were previously provided in the process. More generally, the logic of identifying the appropriate point of care starting from the "Find a Doctor" screen 600 may be based on a host of user information such as, but not limited to, the user's health care needs (i.e., procedure, specialty, condition), existing doctors, demographics, insurance, third-party benefits, and timing, among others.

Exemplary User Scenario #1

By way of example, a user is experiencing a fever and needs to schedule a doctor visit without having previously established a relationship with a primary care physician. In this scenario, the user accesses the application provided by the present disclosure late on a Friday afternoon before a holiday weekend. Once directed to the "Find a Doctor" screen 600, the user may select the "NO" button 602 to indicate that the user is not seeking an appointment with a specific doctor. A subsequent screen (not shown) may ask, "Are you ill or injured?" In this instance, the user selects the "ill" option and is then prompted to select a type of illness from a list of options which may include but is not limited to cold/flu, stomach problems, headaches, other. By way of example, the user selects the "cold/flu" option and is then prompted to identify the necessary time frame of the doctor visit from a list of options which may include, (1) as soon as possible, (2) a week or two, (3) within the month, etc. In response, the user selects the "as soon as possible" option. In this embodiment, the application recognizes that due to the timing of the request, a proximately-located primary care physician does not have availability within the requested time frame. However, the application recognizes that there are several open urgent care facilities and associated doctors that do have short-term availability. Accordingly, the application may present a "results" screen that recommends an urgent care facility as well as a disclaimer of summary information as to the reasoning behind the recommendation. Also, the application then further generates an activation card for display the Home Screen 300 (FIG. 3) that serves as a reminder that the user needs to establish a relationship with a primary care physician. The recommendations and results that are provided to the user may be dependent on a number of different factors. In this regard, another user may input the same information as described in the user scenario above and receive different results or recommendations. For example, a different user could be presented with a results screen indicating that a Tele-medicine service is available with their insurance that can assist with acute illnesses in a short-term time frame. In this instance, the application provides the information regarding the Tele-medicine services in which a user can access a doctor electronically via video conference or otherwise, and then also provides results that identify urgent care facilities which have short term availability as another option.

Exemplary User Scenario #2

By way of another example, a user needs to have a routine colonoscopy from a doctor specializing in the Gastro Intestinal (GI) tract. The user's most recent colonoscopy was 5-6 years earlier and, in a recent appointment, the user's primary care physician recommended the procedure be performed. In this scenario, the user remembers the name of their previous GI doctor and accesses the application provided by the present disclosure to obtain the contact information for this specialist and potentially schedule an appointment. Once directed to the "Find a Doctor" screen 600, the user may select the "YES" button 604 to indicate that the user is seeking an appointment with a specific doctor. A search screen (not shown) is then presented from which the user may search and identify their GI specialist. Similar to the description provided with reference to the medication screen 400 (FIG. 4) above, the search screen is configured to work in conjunction with an unstructured data search component in identifying the user's GI specialist. In this regard, search fields are configured to populate the most relevant GI specialist as the user types. As the possible results are identified, the user is able to select a specific physician. In instances when insurance claim information is available, the user's previous doctors may be presented within the results of the unstructured data search or otherwise.

Once the user in this scenario identifies the relevant GI specialist, another screen (not shown) may prompt the user to select a type of illness from a list of options. For most specialties, the application determines the different types of illnesses that are presented as options based on conditions specific to the identified specialty. Accordingly, the user in this scenario selects colonoscopy from that list as the reason for the doctor visit. The combination of specialty and conditions can then drive subsequent questions as the user may be prompted for preferences and availability for an appointment. Aspects of the present disclosure processes the input received from the user to identify multiple GI specialists available for an appointment. In this scenario, the user's previous GI doctor may be presented as a first option. However, it may be noted that this doctor is more expensive or would incur more out-of-pocket costs than other recommended options. The user selects between the different GI specialists and may then directly set up an appointment from within the application or could contact their health care advisor to setup the appointment. In this regard, an exemplary set of questions that may be presented to the user in selecting a GI specialist is presented in Table 1, below.

TABLE 1

| | |
|---|---|
| Question 1: Who do you need to see or where do you need to go? | Answer options: List of common provider types and "other options." In this example, other options leads to a search type ahead where the user can enter specialty or facility type names or specific doctor and facility names (e.g. Gastroenterology or Dr. John Doe). |
| Question 2: Why do you need to be seen? | Answer options: Common reasons to visit this specialist are listed (e.g. colonoscopy, upper GI (EGD), medication management, etc.). |
| Do you have preferences? | Answer options: Gender, location preferences, years of experience, and the like. |
| When do you need to be seen? | Answer options: As soon as possible, a week or two, within the month, etc.. |

Exemplary User Scenario #3

By way of another example, a user has been experiencing a number of symptoms and suspects that Lyme disease is the cause. However, the user does not know what type of doctor treats Lyme disease. Once directed to the "Find a Doctor" screen 600, the user may select the "NO" button 602 to indicate that the user is not seeking an appointment with a specific doctor. From a subsequent screen (not shown) the user is able to select an option that states: "Let me tell you about my condition." In turn, another screen is presented that enables the user to identify and select Lyme disease as the relevant condition. Once Lyme disease is selected, the user may be prompted as to whether the user has an existing relationship with a primary care doctor. If the user does not have a primary care physician, the system may first direct the user to a primary care doctor in the results (as opposed to a rheumatologists). In this scenario, the user would also be provided with a disclaimer (on an interstitial screen as described further below) noting that a primary care doctor is able to diagnose and treat many issues and are commonly much less expensive than specialists who treat the same diseases. In the event that the user does not have a primary care doctor or chooses to seek out a specialist, the system may identify one or more rheumatologists that is presented to the user.

Figure 7:
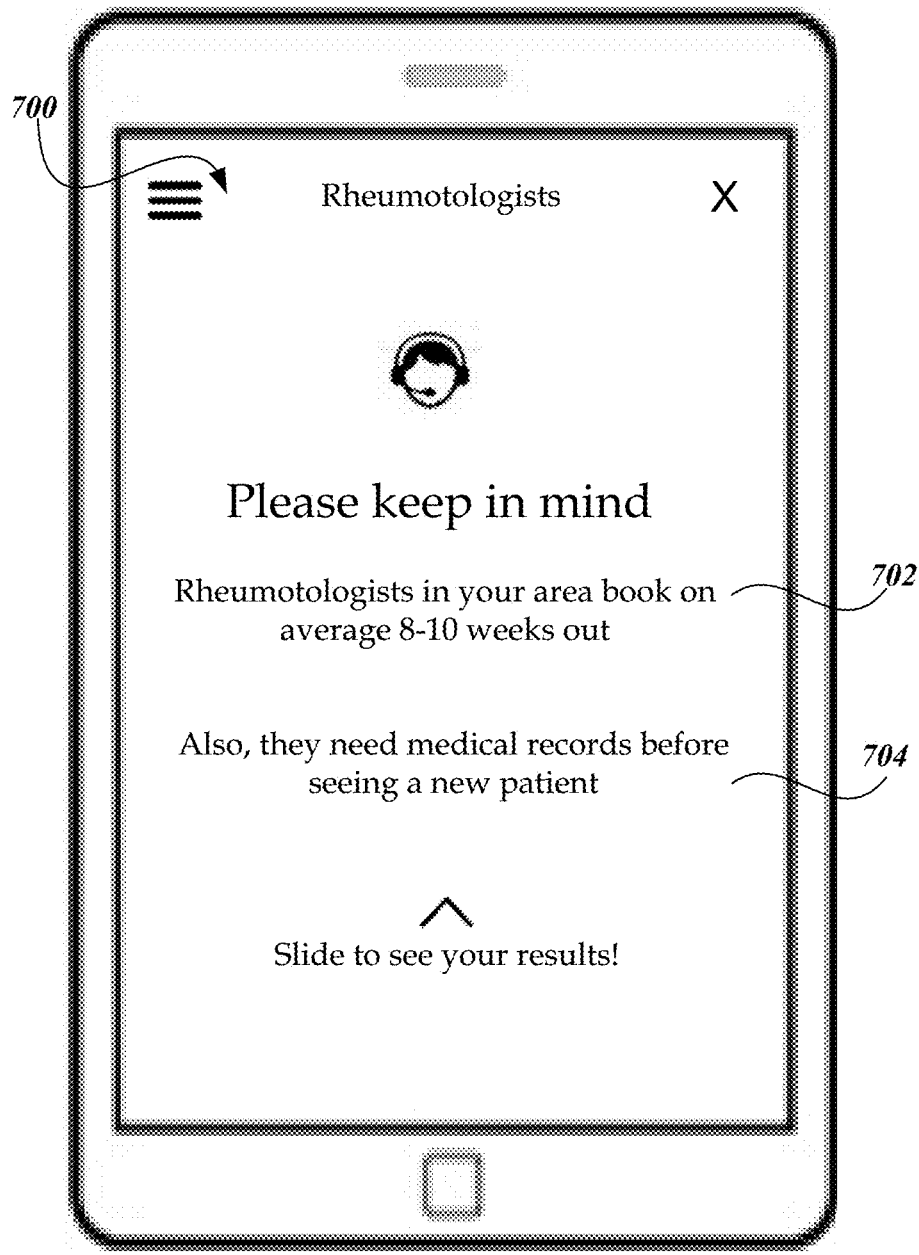
FIG. 7 is a pictorial depiction of an exemplary user interface for interacting with a user obtaining health care information in accordance with the present disclosure.

Now with reference to FIG. 7, an exemplary "interstitial" screen 700 suitable for illustrating additional aspects of the present disclosure is shown. The user may be presented with the specific information on interstitial screen 700 in the Exemplary User Scenario #3 described above. In this regard, the Interstitial screen 700 depicted in FIG. 7 displays the contextual messages 702 and 704 which provide information relevant when a patient visits a rheumatologists. In general, the messages that are presented on the interstitial screen includes information that connects context from the triage questions (as described above with reference to FIG. 6) to results. The Context Engine 248 (FIG. 2) identifies and produces the appropriate messages for display to the user using source data that includes, but is not limited to, the user's search preferences, the requested doctor or facility type, information about the specialty searched, and specific data regarding the doctors in the user's area (e.g. availability, years of practice, etc.). In some embodiments, a message presented on the interstitial screen may call attention to a violation of a user preference that could not be met with the search results. Also, a presented message can outline how alternatives were selected or identify a specific specialty that should be considered. In this regard, a non-exhaustive set of messages that may be presented to the user and their associated contextual category is provided in Table 2 below.

TABLE 2

| TYPE | MESSAGE |
| --- | --- |
| Diagnostic specific context | Only a few doctors in your area focus exclusively on skin cancer |
| Provider specific context | The doctor you selected is no longer in network |
| Provider specific context | The doctor you selected has moved |
| Provider specific context | The prices at the facility you selected have gone up substantially because it was recently purchased by a local hospital system |
| Provider specific context | Rheumatologists can prescribe expensive medications, so contact Compass for a price check if you are prescribed a new medication |
| Plan specific context | You have a maternity program available to you |
| Violation of preferences | There are two male doctors we would recommend. I've also included some female options just in case |
| Results specific context | There are no doctors we would recommend |
| Next actions context | This is a complex surgery. Your health advisor is the best resource to help understand cost and options |

It should be well understood that the examples provided in Table 2 and with reference to FIG. 7 are merely exemplary. In actual embodiments, there are a number of additional contextually relevant messages that may be presented other than those described herein. In this regard, one skilled in the art will recognize that the present disclosure provides a framework for identifying and presenting contextually relevant information to a user and that the specific examples mentioned here are merely representative.

Figure 8:
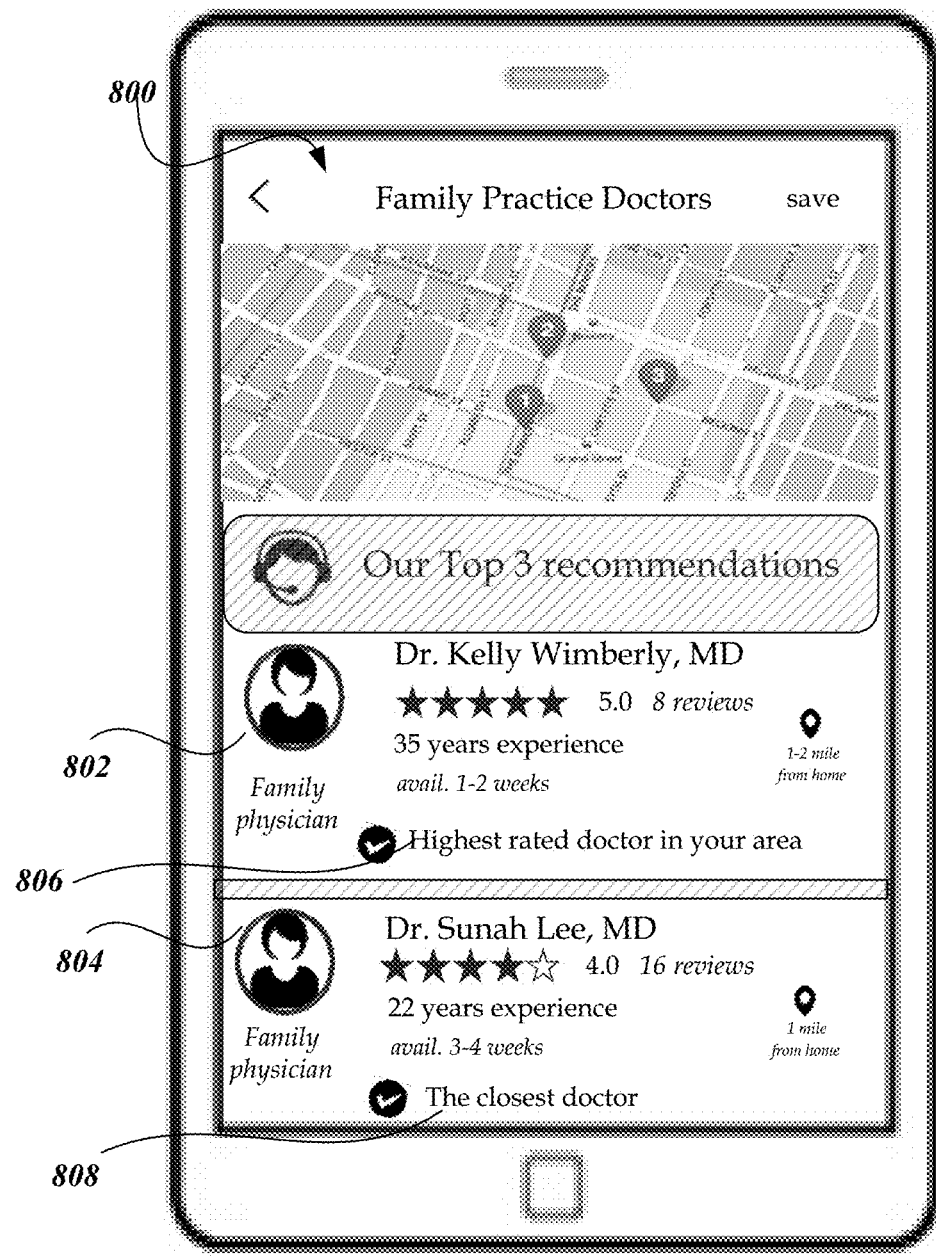
FIG. 8 is a pictorial depiction of an exemplary user interface for interacting with a user obtaining health care information in accordance with the present disclosure.

Now with reference to FIG. 8, an exemplary "results" screen 800 suitable for illustrating additional aspects of the present disclosure is shown. The results screen 800 identifies the doctors in entries 802 and 804 that were identified as being most relevant for an exemplary user search. To access the third or any additional recommended doctor, the user would provide input to scroll down on the results screen 800. Within each provider result in the entries 802 and 804, the user is presented with basic information about the doctor which may include, but is not limited to, name, years of experience, and availability. In addition, the results includes additional pieces of contextual information that, in this example, includes rating, practice type, distance/location, availability, picture, and the like. Many other pieces of contextual information may be provided such as the anticipated out-of-pocket expenses that would be incurred when utilizing the identified practitioner for a particular procedure. Accordingly, the set of information presented on the "results" screen 800 depicted in FIG. 8 is merely representative and should be construed as exemplary. However, in a preferred embodiment, the primary reason that a medical care provider is being recommended is identified. This aspect of the present disclosure is depicted in FIG. 8, with the data elements 806 and 808 identifying the contextual reason as to why the identified medical provider is being recommended. In most instances, this context provides a superlative about the medical care provider. However, in other instances, negative contextual information may be communicated to the user on the results page 800. For example, the fact that a medical care provider is excessively expensive, not board certified, or has a disciplinary record may be displayed on the results screen 800. In another embodiment, aspects of the present disclosure provide a warning context to the user when providing a recommendation. The warning context may provide context in a number of different instances such as when certain information is unavailable. In the regard, the warning context could state that "we don't know if this doctor is in-network" or "we do not know if this doctor does this procedure." The user may select between the recommended doctors presented on the results screen 800. Then, the user may directly set up an appointment from within the application or could contact their health care advisor to setup the appointment.

Figure 9:
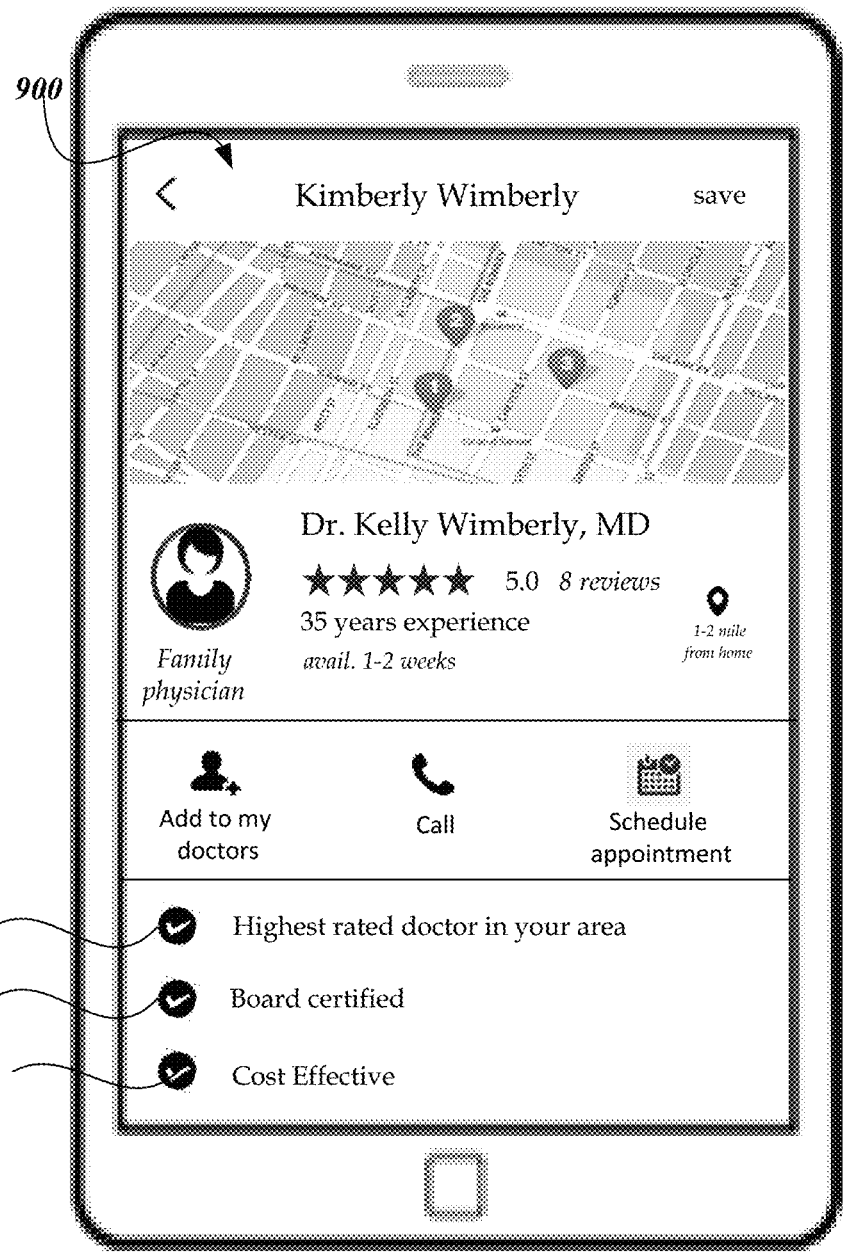
FIG. 9 is a pictorial depiction of an exemplary user interface for interacting with a user obtaining health care information in accordance with the present disclosure.

Now with reference to FIG. 9, an exemplary "medical provider" screen 900 suitable for illustrating additional aspects of the present disclosure is shown. In the scenario described above with reference to FIG. 8, the user is presented with a list of three (3) recommended medical care providers. In this regard, the user may select one of the entries on the results screen 800 (FIG. 8) to "drill down" and obtain additional information about a specific provider. So, in this example, the user selected entry 802 from the results screen 800 (FIG. 8) in order to access additional information about Dr. Kelly Wimberly. In response, a number of new pieces of contextual information are presented in entries 902, 904, and 906. Typically all of the contextual data associated with a particular medical care provider is presented on the "medical provider" screen including an negative or warning contextual data. Also, by navigating to the screen 900 a convenient mechanisms is provided for contacting and/or scheduling an appointment with user's health care provider.

Figure 10:
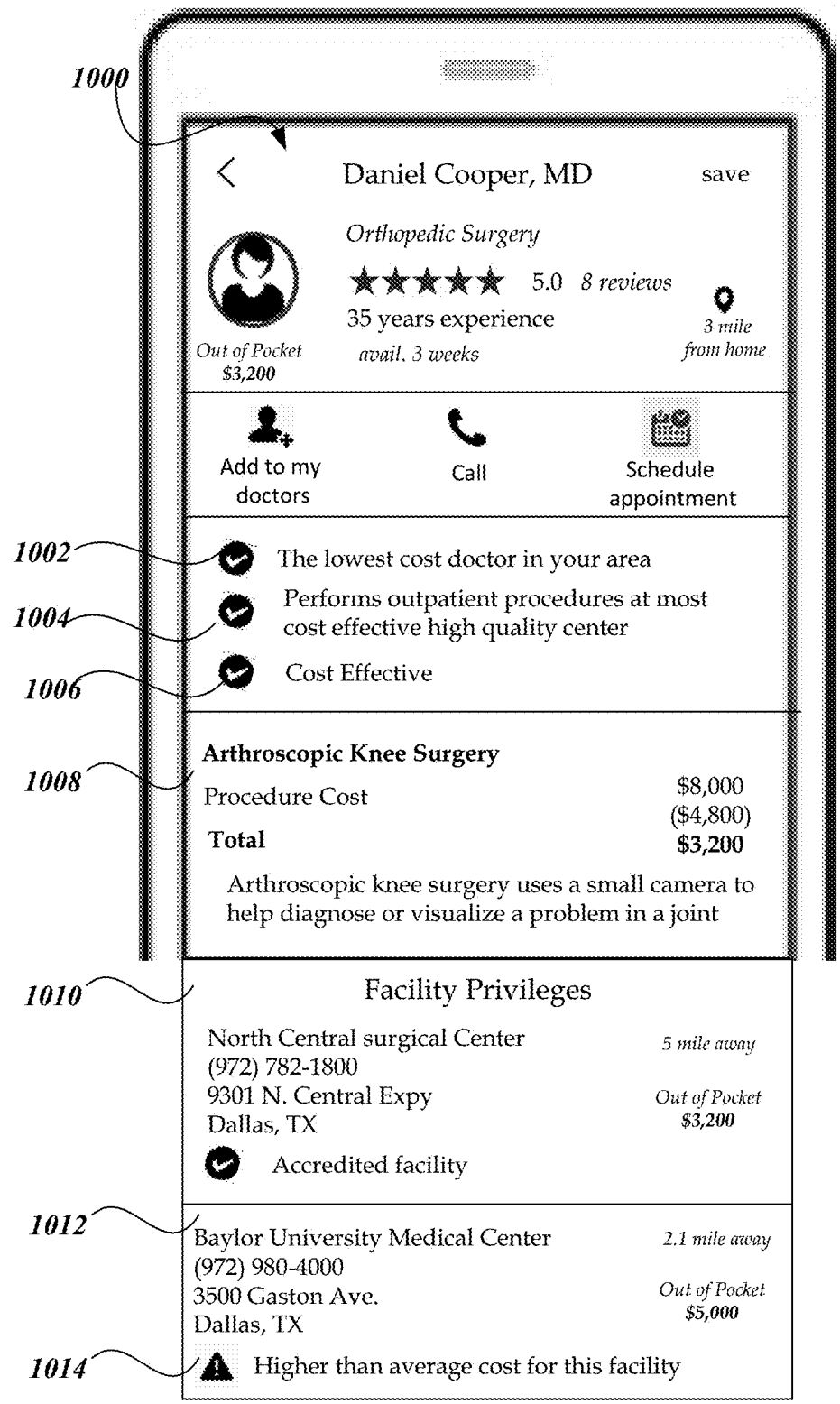
FIG. 10 is a pictorial depiction of an exemplary user interface for interacting with a user obtaining health care information in accordance with the present disclosure.

Now with reference to FIG. 10, another exemplary "medical provider" screen 1000 suitable for illustrating additional aspects of the present disclosure is shown. In this instance, the user may utilize the application provided by the present disclosure to find an orthopedist for an arthroscopic knee surgery. The initial appointment and subsequent surgery may be scheduled through the application provided by the present disclosure. Similar to the description provided above, a decision tree of questions may be employed to obtain specific information about the medical procedure from the user. Based on this input and other data, a result set of medical care providers recommended to perform the procedure is generated and communicated. Different types of information, including interstitial data, may be communicated about the medical care providers in the result set. In this example, the user may select between providers in the result set and be presented with the medical provider screen 1000 to obtain detailed information about the selected provider. This medical care provider information and associated data may also be saved and later recalled on demand. So, in this example, the user selected Dr. Daniel Cooper and is presented with various pieces of information about the selected provider including the contextual information in entries 1002, 1004, and 1006. In this regard, one or more pieces of contextual information depicted in FIG. 10 may be presented on an interstitial screen (not shown) in the process of selecting this provider.

When a user provides input about the procedure, additional context may be communicated to the user about the medical care provider and the identified procedure. In this regard, the costs associated with the arthroscopic knee surgery using the selected provider may be presented in entry 1008. This cost data may be presented along with summary information that describes the relevant medical procedure. Also, the facilities in which the selected doctor is credentialed may be identified in entries 1010 and 1012, respectively. Detailed contextual data may be provided about the these facilities. This information enables a user to determine how the selection of a particular facility affects costs as shown in FIG. 10. A number of different pieces of contextual data associated with a particular medical facility may be presented on the screen 1000 including negative or warning contextual data. In the example depicted in FIG. 10, a piece of contextual data that serves as a warning about using a particular facility is presented in entry 1014. By providing this type of information, aspects of the present disclosure provide users with detailed information about their medical care so that users may make more informed choices as a health care consumer.

While the preferred embodiment of the present disclosure has been illustrated and described, it will be appreciated that various changes can be made therein without departing from the spirit and scope of the disclosed subject matter.

The embodiments of the disclosure in which an exclusive property or privilege is claimed are defined as follows:

1. A method for applying computer technology that dynamically filters content based on a plurality of constraints to produce a hyper-personalized recommendation for a user regarding health care services that is controllably permitted to depart from a first set of the constraints, the method comprising:
   a server hosting a context engine and a knowledge base, wherein the knowledge base stores attributes of a plurality of medical care providers, the medical care provider attributes including location data for the medical care providers, accepted health insurance data for the medical care providers, specialty data for the medical care providers, and pricing data for the medical care providers;
   the server receiving a request from the user via an interface for a recommendation of one or more medical care providers to service a medical need of the user;
   the server defining a first set of constraints and a second set of constraints based on the received request and a user profile, wherein the second set of constraints is more relaxed than the first set of constraints, the first and second sets of constraints for finding a medical care provider within the knowledge base for servicing the medical need of the user, the constraints within the first and second sets comprising data about the medical need, data about a location for the user, data about health insurance of the user, and data about desired characteristics for the sought medical care provider;
   the context engine autonomously applying the first and second sets of constraints to the knowledge base, wherein the autonomously applying step comprises:
      filtering the medical care provider attributes based on the first set of constraints and the second set of constraints to gather contextually relevant data points about (1) one or more medical care providers from the knowledge base who satisfy the first set of constraints and (2) a plurality of medical care providers from the knowledge base who satisfy the second set of constraints;
      identifying one or more medical care providers from the knowledge base who satisfy the first set of constraints based on the filtered medical care provider attributes;
      identifying a plurality of medical care providers from the knowledge base who satisfy the second set of constraints based on the filtered medical care provider attributes;
      determining whether to use a constraint exception for the first set of constraints based on defined criteria; and
      in response to a determination to use the constraint exception, creating a list of contextually relevant medical care providers for the request from the identified medical care providers who satisfy the second set of constraints;
      weighting the contextually relevant data points for the contextually relevant medical care providers;
      ranking the contextually relevant medical care providers based on an estimation of best fit for the user accounting for the weighted contextually relevant data points; and
      determining a primary contextual reason for including the top ranked medical care provider on the list, wherein the primary contextual reason identifies information derived from the knowledge base about the top ranked medical care provider that is related to at least one of the constraints; and
   the server providing data representing (1) the top ranked medical care provider from among the ranked medical care providers and (2) the determined primary contextual reason to a user interface, wherein the user interface displays the top-ranked medical care provider along with the determined primary contextual reason as a part of a recommendation in response to the request.

2. The method of claim 1, further comprising:
   the server dynamically interacting with the interface to obtain information describing the medical need and related preferences by (1) selecting a question from a decision tree of questions to prompt the user for information describing the medical need and related preferences, (2) receiving an answer from the user to the selected question via the interface, and (3) repeating the question selecting and answer receiving steps for a plurality of new questions, wherein the new questions are selected based on previously received answers; and the server defining the constraints based on the received answers.

3. The method of claim 1, wherein the user interface comprises a graphical user interface (GUI) of a computing device the method further comprising;
the server generating a summary content via the context engine for display on the GUI.

4. The method of claim 3, wherein the summary content provides an average cost for servicing the medical need in an area corresponding to the user's location data as reflected by the constraints.

5. The method of claim 1, further comprising the server continuously evolving the medical care provider attributes in the knowledge base and data within the user profile based on new information available from sources that include insurance provider databases.

6. The method of claim 1, wherein the server creates an attribute set associated with the user, the attribute set employed by the context engine to generate an activation card for display on a graphical user interface (GUI).

7. A health care recommendation system that dynamically filters content based on a plurality of constraints to produce a hyper-personalized recommendation for a user regarding health care services that is controllably permitted to depart from a first set of the constraints, the system comprising:
a server, the server including a context engine and a knowledge base; and
a mobile application for execution by a computing device that is connectable with the server via a network, the mobile application configured to interact with the user via a plurality of graphical user interfaces (GUIs);
wherein the knowledge base stores attributes of a plurality of medical care providers, the medical care provider attributes including location data for the medical care providers, accepted health insurance data for the medical care providers, specialty data for the medical care providers, and pricing data for the medical care providers;
wherein the mobile application receives user input via one or more of the GUIs that causes the computing device to send a request to the server for a recommendation of one or more medical care providers to service a medical need of the user;
wherein the server, in response to the request, defines a first set of constraints and a second set of constraints based on the request and a user profile, wherein the second set of constraints is more relaxed than the first set of constraints, the first and second sets of constraints for finding a medical care provider within the knowledge base for servicing the medical need of the user, the constraints within the first and second sets comprising data about the medical need, data about a location for the user, data about health insurance of the user, and data about desired characteristics for the sought medical care provider;
wherein the context engine autonomously:
filters the medical care provider attributes based on the first set of constraints and the second set of constraints to gather contextually relevant data points about (1) one or more medical care providers from the knowledge base who satisfy the first set of constraints and (2) a plurality of medical care providers from the knowledge base who satisfy the second set of constraints;
identifies one or more medical care providers from the knowledge base who satisfy the first set of constraints based on the filtered medical care provider attributes;
identifies a plurality of medical care providers from the knowledge base who satisfy the second set of constraints based on the filtered medical care provider attributes;
determines whether to use a constraint exception for the first set of constraints based on defined criteria; and
in response to a determination to use the constraint exception, creates a list of contextually relevant medical care providers for the request from the identified medical care providers who satisfy the second set of constraints;
weights the contextually relevant data points for the contextually relevant medical care providers;
ranks the contextually relevant medical care providers based on an estimation of best fit for the user accounting for the weighted contextually relevant data points; and
determines a primary contextual reason for including the top ranked medical care provider on the list, wherein the primary contextual reason identifies information derived from the knowledge base about the top ranked medical care provider that is related to at least one of the constraints;
wherein the server provides data representing (1) the top ranked medical care provider from among the ranked medical care providers and (2) the determined primary contextual reason to the mobile application via the network; and
wherein the mobile application causes at least one of the GUIs to display the top-ranked medical care provider along with the determined primary contextual reason as a part of a recommendation in response to the request.

8. The health care recommendation system of claim 7, wherein the context engine further generates a summary content for display on at least one of the GUIs.

9. The health care recommendation system of claim 8, wherein the summary content provides an average cost for servicing the medical need in an area corresponding to the user's location data as reflected by the constraints.

10. The health care recommendation system of claim 7, wherein the medical care provider attributes in the knowledge base and data in the user profile are continuously evolving based on new information available from sources that include insurance provider databases.

11. The health care recommendation system of claim 7, wherein the server creates an attribute set associated with the user, the attribute set employed by the context engine to generate an activation card on at least one of the GUIs.

12. The health care recommendation system of claim 7, wherein the server comprises a plurality of servers that are part of a cloud computing network.

13. The method of claim 1, wherein a first result set includes the identified one or more medical care providers from the knowledge base who satisfy the first set of constraints based on the filtered medical care provider attributes, wherein a second result set includes the identified medical care providers from the knowledge base who satisfy the second set of constraints based on the filtered medical care provider attributes, where the second result set is an expanded result set relative to the first result set; and
wherein the constraint exception determining step comprises choosing between the first result set and the second result set according to the defined criteria.

14. The method of claim 1, further comprising limiting the ranking step so that medical care providers who do not satisfy the constraints are not ranked.

15. The method of claim 1, wherein the determined primary contextual reason comprises a doctor being deemed cost effective from among the contextually relevant medical care providers.

16. The method of claim 1, wherein the medical care provider attributes in the knowledge base include ratings information about the medical care providers, and wherein the determined primary contextual reason comprises a doctor being deemed the most highly-rated from among the contextually relevant medical care providers who are known to specialize in serving the user's medical need.

17. The method of claim 1, wherein the medical care provider attributes in the knowledge base include years of experience data for the medical care providers.

18. The method of claim 1, wherein the medical care provider attributes in the knowledge base include timeframe availability data for the medical care providers, and wherein the constraints include timeframe preferences for the user.

19. The method of claim 1, wherein the autonomously applying step comprises determining a primary contextual reason for including the second-ranked medical care provider on the list, wherein the primary contextual reason for the second-ranked medical care provider identifies information derived from the knowledge base about the second-ranked medical care provider that is related to at least one of the constraints; and
   wherein the providing step comprises the server providing data representing the second-ranked medical care provider from among the ranked medical care providers and the determined primary contextual reason for the second-ranked medical care provider to the user interface, wherein the user interface displays, as a part of the recommendation in response to the request, (1) the top-ranked medical care provider along with the determined primary contextual reason for the top-ranked medical care provider and (2) the second-ranked medical care provider along with the determined primary contextual reason for the second-ranked medical care provider.

20. The method of claim 1, wherein the autonomously applying step comprises determining warning context corresponding to at least one of the medical care providers on the list; and
   the server providing the warning context to the user interface for display thereon in relation the corresponding at least one medical care provider.

21. The method of claim 20, wherein the warning context identifies that it is unknown whether the corresponding at least one medical care provider is in-network for the user's health insurance.

22. The method of claim 1, wherein the user interface includes a selectable option corresponding to a medical care provider recommended via the user interface for causing a computing device on which the user interface is displayed to call a phone number for the corresponding medical care provider.

23. The method of claim 1, wherein the user interface includes a selectable option corresponding to a medical care provider recommended via the user interface for scheduling an appointment with the corresponding medical care provider.

24. The method of claim 1, wherein the server comprises a plurality of servers.

25. The health care recommendation system of claim 7, further comprising:
   the server and the mobile application dynamically interact with each other to obtain information describing the medical need by (1) the server selecting a question from a decision tree of questions to prompt the user for information describing the medical need, (2) the mobile application receiving an answer from the user to the selected question and providing the received answer to the server, and (3) repeating the question selecting and answer receiving and providing operations for a plurality of new questions, wherein the new questions are selected based on previously received answers; and
   wherein the server defines the constraints based on the received answers.

26. The health care recommendation system of claim 7, wherein a first result set includes the identified one or more medical care providers from the knowledge base who satisfy the first set of constraints based on the filtered medical care provider attributes, wherein a second result set includes the identified medical care providers from the knowledge base who satisfy the second set of constraints based on the filtered medical care provider attributes, where the second result set is an expanded result set relative to the first result set; and
   wherein the context engine determines whether to use the constraint exception by choosing between the first result set and the second result set according to the defined criteria.

27. The health care recommendation system of claim 7, wherein the context engine limits the rank operation so that medical care providers who do not satisfy the constraints are not ranked.

28. The health care recommendation system of claim 7, wherein the determined primary contextual reason comprises a doctor being the deemed cost effective from among the contextually relevant medical care providers.

29. The health care recommendation system of claim 7, wherein the medical care provider attributes in the knowledge base includes ratings information about the medical care providers, and wherein the determined primary contextual reason comprises a doctor being deemed the most highly-rated from among the contextually relevant medical care providers who are known to specialize in serving the user's medical need.

30. The health care recommendation system of claim 7, wherein the medical care provider attributes in the knowledge base include years of experience data for the medical care providers.

31. The health care recommendation system of claim 7, wherein the medical care provider attributes in the knowledge base include timeframe availability data for the medical care providers, and wherein the constraints include timeframe preferences for the user.

32. The health care recommendation system of claim 7, wherein the context engine determines a primary contextual reason for including the second-ranked medical care provider on the list, wherein the primary contextual reason for the second-ranked medical care provider identifies information derived from the knowledge base about the second-ranked medical care provider that is related to at least one of the constraints; and
   wherein the server provides data representing the second-ranked medical care provider from among the ranked medical care providers and the determined primary contextual reason for the second-ranked medical care provider to the mobile application via the network; and wherein the mobile application causes at least one of the GUIs to display, as a part of the recommendation in response to the request, (1) the top-ranked medical care provider along with the determined primary contextual reason for the top-ranked medical care provider and (2) the second-ranked medical care provider along with the determined primary contextual reason for the second-ranked medical care provider.

33. The health care recommendation system of claim 7, wherein the context engine determines warning context corresponding to at least one of the medical care providers on the list; and wherein the server provides the warning context to the mobile application via the network for display on at least one of the GUIs in relation the corresponding at least one medical care provider.

34. The health care recommendation system of claim 33, wherein the warning context identifies that it is unknown whether the corresponding at least one medical care provider is in-network for the user's health insurance.

35. The health care recommendation system of claim 7, wherein at least one of the GUIs that displays a recommended medical care provider includes a selectable option corresponding to the recommended medical care provider for causing the computing device to call a phone number for the recommended medical care provider.

36. The health care recommendation system of claim 7, wherein at least one of the GUIs that displays a recommended medical care provider includes a selectable option corresponding to the recommended medical care provider for scheduling an appointment with the recommended medical care provider.

* * * * *